(12) United States Patent
Poss et al.

(10) Patent No.: US 7,544,737 B2
(45) Date of Patent: Jun. 9, 2009

(54) MACROMOLECULAR KETOALDEHYDES

(75) Inventors: Mitchell J. Poss, Antioch, IL (US); Henk Blom, Mundelein, IL (US); Alex Odufu, Hoffman Estates, IL (US); Robert Smakman, Nigtevecht (NL)

(73) Assignees: Baxter International Inc., Deerfield, IL (US); Baxter Healthcare S.A., Zurich (CH)

( * ) Notice: Subject to any disclaimer, the term of this patent is extended or adjusted under 35 U.S.C. 154(b) by 0 days.

(21) Appl. No.: 10/987,331

(22) Filed: Nov. 12, 2004

(65) Prior Publication Data
US 2005/0131141 A1    Jun. 16, 2005

Related U.S. Application Data

(62) Division of application No. 10/376,095, filed on Feb. 28, 2003, now Pat. No. 6,861,473.

(51) Int. Cl.
| | |
|---|---|
| C08F 220/12 | (2006.01) |
| C08L 29/00 | (2006.01) |
| C08F 16/34 | (2006.01) |
| C08F 16/36 | (2006.01) |
| C08F 12/02 | (2006.01) |
| C08F 112/02 | (2006.01) |

(52) U.S. Cl. .................. 524/818; 526/315; 526/316; 526/346

(58) Field of Classification Search .............. 524/818; 526/315, 316, 346
See application file for complete search history.

(56) References Cited

U.S. PATENT DOCUMENTS

| | | | |
|---|---|---|---|
| 3,531,463 | A | 9/1970 | Gustafson et al. |
| 3,669,878 | A | 6/1972 | Marantz et al. |
| 3,669,880 | A | 6/1972 | Marantz et al. |
| 3,742,946 | A | 7/1973 | Grossman |
| 3,794,584 | A | 2/1974 | Kunin et al. |
| 3,850,835 | A | 11/1974 | Marantz et al. |
| 3,933,753 | A * | 1/1976 | Kuntz et al. .......... 525/242 |

(Continued)

FOREIGN PATENT DOCUMENTS

DE        4338124        5/1995

(Continued)

OTHER PUBLICATIONS

Floyd et al., *The oxidation of acetophenones to arylglyoxals with aqueous hydrobromic acid in dimethyl sulfoxide*, J. Org. Chem., vol. 50, No. 25, 1985, pp. 5022-5027.

(Continued)

*Primary Examiner*—William K Cheung
(74) *Attorney, Agent, or Firm*—Paula J. Kelly; K & L Gates LLP

(57) ABSTRACT

Methods of producing macromolecular compositions and using same are provided. The method includes preparing a resin material; forming an acetyl group on the resin material; and oxidizing the acetyl group via a one-step reaction including reacting a sulfoxide and an acid with the acetyl group to form a ketoaldehyde group. The macromolecular compositions are capable of removing an effective amount of one or more constituents from a physiological solution, such as urea during dialysis therapy.

2 Claims, 1 Drawing Sheet

U.S. PATENT DOCUMENTS

| | | | |
|---|---|---|---|
| 3,989,622 | A | 11/1976 | Marantz et al. |
| 3,997,706 | A | 12/1976 | Galeazzi |
| 4,012,317 | A | 3/1977 | Kuntz et al. |
| 4,043,979 | A | 8/1977 | Cram |
| 4,064,042 | A | 12/1977 | Kunin |
| 4,140,652 | A | 2/1979 | Korshak et al. |
| 4,178,241 | A | 12/1979 | Sullivan et al. |
| 4,182,750 | A | 1/1980 | Sullivan et al. |
| 4,202,775 | A | 5/1980 | Abe et al. |
| 4,246,351 | A | 1/1981 | Miyake et al. |
| 4,281,233 | A | 7/1981 | Coupek et al. |
| 4,376,707 | A | 3/1983 | Lehmann |
| 4,392,963 | A | 7/1983 | Perl et al. |
| 4,425,237 | A | 1/1984 | Abe et al. |
| 4,460,555 | A | 7/1984 | Thompson |
| 4,543,365 | A | 9/1985 | Itagaki et al. |
| 4,571,390 | A | 2/1986 | Sakagami et al. |
| 4,650,587 | A | 3/1987 | Polak et al. |
| 4,661,526 | A | 4/1987 | Ford |
| 4,675,384 | A | 6/1987 | Dromard et al. |
| 4,677,135 | A | 6/1987 | Mishima |
| 4,715,961 | A | 12/1987 | Mishima |
| 4,721,652 | A | 1/1988 | Takai et al. |
| 4,814,077 | A | 3/1989 | Furuyoshi et al. |
| 4,897,200 | A * | 1/1990 | Smakman ............... 210/692 |
| 4,908,405 | A | 3/1990 | Bayer et al. |
| 5,051,185 | A | 9/1991 | Watanabe et al. |
| 5,110,875 | A | 5/1992 | Jaxa-Chamiec et al. |
| 5,112,922 | A | 5/1992 | Jaxa-Chamiec et al. |
| 5,151,192 | A | 9/1992 | Matkovich et al. |
| 5,218,004 | A | 6/1993 | Meteyer |
| 5,258,503 | A | 11/1993 | Yokohari et al. |
| 5,300,628 | A | 4/1994 | Honda |
| 5,431,807 | A | 7/1995 | Frechet et al. |
| 5,446,104 | A | 8/1995 | Handlin, Jr. et al. |
| 5,460,725 | A | 10/1995 | Stringfield |
| 5,514,281 | A | 5/1996 | Boos et al. |
| 5,522,996 | A | 6/1996 | Brownstein et al. |
| 5,536,412 | A | 7/1996 | Ash |
| 5,624,880 | A | 4/1997 | Steffier |
| 5,677,126 | A | 10/1997 | Bensimon et al. |
| 5,736,520 | A * | 4/1998 | Bey et al. ............... 514/19 |
| 5,919,369 | A | 7/1999 | Ash |
| 6,087,300 | A | 7/2000 | Davankov et al. |
| 6,114,466 | A | 9/2000 | Davankov et al. |
| 6,127,311 | A | 10/2000 | Davankov et al. |
| 6,133,393 | A | 10/2000 | Davankov et al. |
| 6,136,424 | A | 10/2000 | Davankov et al. |
| 6,153,707 | A | 11/2000 | Davankov et al. |
| 6,156,851 | A | 12/2000 | Davankov et al. |
| 6,159,377 | A | 12/2000 | Davankov et al. |
| 6,217,901 | B1 | 4/2001 | Perrott et al. |
| 6,303,702 | B1 | 10/2001 | Davankov et al. |
| 6,334,984 | B1 | 1/2002 | Pagani et al. |

FOREIGN PATENT DOCUMENTS

| | | |
|---|---|---|
| EP | 0 217 062 | 4/1987 |
| JP | 56141833 | 11/1981 |
| JP | 57081829 | 5/1982 |
| JP | 57130545 | 8/1982 |
| JP | 60137433 | 7/1985 |
| JP | 61171506 | 8/1986 |
| JP | 62033539 | 2/1987 |
| JP | 63059353 | 3/1988 |
| JP | 02221224 | 9/1990 |
| JP | 09302034 | 11/1997 |
| WO | WO 93/17989 | 9/1993 |

OTHER PUBLICATIONS

Smakman et al., *Urea removal by means of direct binding*, Clinical Nephrology, vol. 26 Suppl. No. 1—1986, pp. S58-S62.

Lehmann et al., *How to Catch Urea? Considerations on Urea Removal from Hemofiltrate*, Artificial Organs, vol. 5, No. 3, 1981, pp. 278-285.

McCaldin, D.J., *The Chemistry of Ninhydrin*, Chem. Rev., vol. 60, 1960, pp. 39-51.

Odian, G., *Principles of Polymerization, Third Edition*, John Wiley and Sons, New York, 1991 p. 302.

Solomons, T.W.G., Organic Chemistry, Third Edition, John Wiley and Sons, New York, 1984, p. 478-480.

Ibid., p. 480-482.

Kornblum et al., *A New and Selective Method of Oxidation*, J. Am. Chem. Soc., vol. 79, 1957, p. 6562.

Furniss et al., *Vogel's Textbook of Practical Organic Chemistry*, Fifth Edition, Prentice Hall, London, 1989, p. 1052.

Rumpf et al., Chem. Ing. Tech., vol. 43, 1971, p. 367. (non-English).

Y. Nakada c.s., Agric. Biol. Chem., vol. 42, 1978, pp. 1365-1373, CA 1978:563290.

Rectanus et al., Polymer Bull. (Berlin), vol. 32, 1994, pp. 373-380, CA 1994: 410024.

Mahato et al., *A new synthetic route to aromatic Glyoxals*, Indian Chem. J Sect. B, vol. 25B, Issue 12, 1986, p. 1263.

Renal International, Marketing Literature, The BetaSorb device; published before Feb. 14, 2000.

Cushman et al., *Synthesis of Trifluoromethylated Pyrazine-Containing Nitrogen Heterocycles from Trifluoropyruvaldehyde and Ortho-Diamines: Scope and Regochemistry*, J. Org. Chem. 1988, vol. 53, 5088-5092.

* cited by examiner

MACROMOLECULAR KETOALDEHYDES

CROSS REFERENCES TO RELATED APPLICATIONS

This patent application is a divisional of U.S. application Ser. No. 10/376,095 filed on Feb. 28, 2003, now U.S. Pat. No. 6,861,473 the disclosure of which is herein incorporated by reference.

BACKGROUND OF THE INVENTION

The present invention relates generally to macromolecular compositions. More specifically, the present invention relates to methods of making and using macromolecular ketoaldehyde compositions that have chemical binding properties.

In general, materials are known and used to remove constituents from fluids for a number of different applications including, for example, industrial, recreational, therapeutic, diagnostic and/or the like. For example, cationic polymers, anionic polymers and combinations thereof are typically used to purify a variety of different aqueous streams, such as industrial process streams, via ion exchange, flocculation or other suitable mechanism. Other materials are generally known as sorbent materials. The physiochemical properties of these types of materials enable them to remove suitable types of constituents from fluid via adsorption, absorbtion, chemisorption, chemical binding and/or other suitable mechanisms.

In general, polymeric materials are known in the art that are capable of removing nitrogen-containing compounds, such as urea, creatinine, proteins, amino acids, glyco-proteins and/or other metabolic waste in solution. These types of materials contain a functional group(s) that chemically bind with urea or other like compounds. For example, U.S. Pat. Nos. 3,933,753 and 4,012,317 disclose an alkenylaromatic polymer containing phenylglyoxal that can function to chemically bind urea. As disclosed, the process for making the glyoxal-functionalized polymer, in general, includes the preparation of a poly-p-vinylacetophenone. Next, a phenacyl bromide is formed. This is followed by a separate step that includes the oxidation of the poly-p-vinylphenacetyl halide to form the phenylglyoxal groups. See, for example, U.S. Pat. No. 3,933,753, columns 7 and 8.

Another example of a polymeric material capable of removing urea or the like in solution is disclosed in U.S. Pat. No. 4,897,200. This material includes a tricarbonyl functionality commonly known as ninhydrin. The general formula of the polymeric material (P-ninhydrin) is shown below:

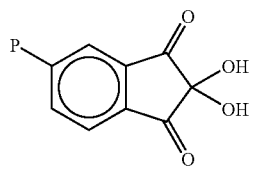

The ninhydrin-containing material may produce better urea uptake levels as compared to, for example, the glyoxal-containing materials discussed above. However, the ninhydrin product is expensive to make due, in part, to the numerous reaction steps necessary to carry out the reaction.

A need, therefore, exists to provide macromolecular compositions made from improved methods with chemical binding properties that can be effective even under physiological conditions and that can be readily and easily made at reduced costs, and easily adapted to existing systems, such as therapeutic system.

SUMMARY OF THE INVENTION

The present invention relates to macromolecular compositions. In particular, the present invention relates to improved methods of making and using macromolecular compositions that have chemical binding properties. The macromolecular compositions of the present invention include macromolecular ketoaldehydes that can chemically bind with one or more suitable constituents of any suitable fluid at enhanced uptake levels. As used herein, the term "macromolecular composition" or other like terms means a large molecule, such as a molecule that has a molecular weight greater than 1000 amu including, for example, synthetic polymers, natural polymers, and/or the like.

The present invention provides processes for producing macromolecular compositions. The macromolecular composition can include a composition prepared via a route of suitable conversions from, for example, a (co)polymerisate of an ethylenically unsaturated compound, such as an aromatic vinyl monomer; a polycondensate, such as obtained, for example, from a Friedel Crafts reactions of aromatic compounds; a natural macromolecular material and modifications thereof; a macromolecular material, such as carbon or other suitable macromolecular product prepared by pyrolysis; an inorganic material, such as silica, alumina, zeolite, sodium aluminum silicates or the like; or combinations thereof. For example, the preparation of macromolecular composition can result in the formation of a resin material composed of crosslinked polystyrene. The macromolecular composition may have a relatively high internal surface area.

The process of the present invention includes the acetylation of the macromolecular composition. This results in the formation of an acetylated macromolecular composition, such as an acetylated polystyrene resin.

Oxidation of the macromolecular composition is performed subsequent to acetylation, thus resulting in the formation of the ketoaldehyde group. In an embodiment of the present invention, the oxidation is performed in a single reaction step. This step includes mixing the acetylated composition with an oxidizing solvent, such as dimethylsulfoxide and/or the like to form a reaction mixture. An acid, such as a hydrohalic acid including hydrobromic acid and/or the like is added to the reaction mixture, thus converting the acetyl groups into the ketoaldehyde groups. Applicants believe that the process of the present invention results in macromolecular ketoaldehydes with enhanced functionalization. This can faciliate the binding capabilities of the composition with respect to, for example, anions, molecules or radicals containing heteroatoms with free electron pairs, such as sulfur, nitrogen, oxygen, such as urea, creatinine, uric acid, β-2 microglobulin, proteins similar to β-2 microglobulin, other like metabolic waste, other suitable biological matter and/or other suitable constituent.

In an embodiment, the macromolecular ketoaldehydes of the present invention include a ketoaldehyde. Preferably, the ketoaldehyde is a phenylglyoxal. In an embodiment, the ketoaldehyde has a phenyl group and an α-ketoaldehyde group.

The macromolecular ketoaldehyde compositions of the present invention can be effectively utilized in a variety of different applications even under physiological conditions. For example, the macromolecular compositions of the present invention can be utilized to remove urea and/or the like from any suitable fluid at effective uptake levels. Urea removal or removal of any nucleophile is due to the reactive binding between the ketoaldehydes of the macromolecular composition and one or both nitrogen atoms of urea or one or more nitrogen atoms associated with any suitable nucleophile.

This can be particularly beneficial as applied during regenerative dialysis therapy where the dialysate is regenerated prior to reuse, such as recirculation into, through and out of a patient's peritoneal cavity during continuous flow peritoneal dialysis. In this regard, the macromolecular compositions of the present invention can be adapted in any suitable way to remove at least a portion of urea, other suitable metabolic waste, suitable other biological matter and the like from the dialysate prior to reuse. It should be appreciated that the macromolecular compositions of the present invention can be utilized in a variety of different and suitable applications with respect to and in addition to dialysis therapy.

An advantage of the present invention is to provide improved methods for making macromolecular compositions.

Another advantage of the present invention is to provide improved materials, devices, apparatuses and systems that utilize macromolecular ketoaldehydes made according to an embodiment of the present invention.

Yet another advantage of the present invention is to provide improved macromolecular phenylglyoxals that can chemically bind urea and/or the like.

Yet still another advantage of the present invention is to provide improved macromolecular materials that can chemically bind urea and/or the like under physiological conditions.

A further advantage of the present invention is to provide improved macromolecular compositions that can remove urea and/or the like from solutions used during medical therapy, such as dialysis.

Additional features and advantages of the present invention are described in, and will be apparent from, the following Detailed Description of the Invention and the figures.

DETAILED DESCRIPTION OF THE INVENTION

Figure 1:
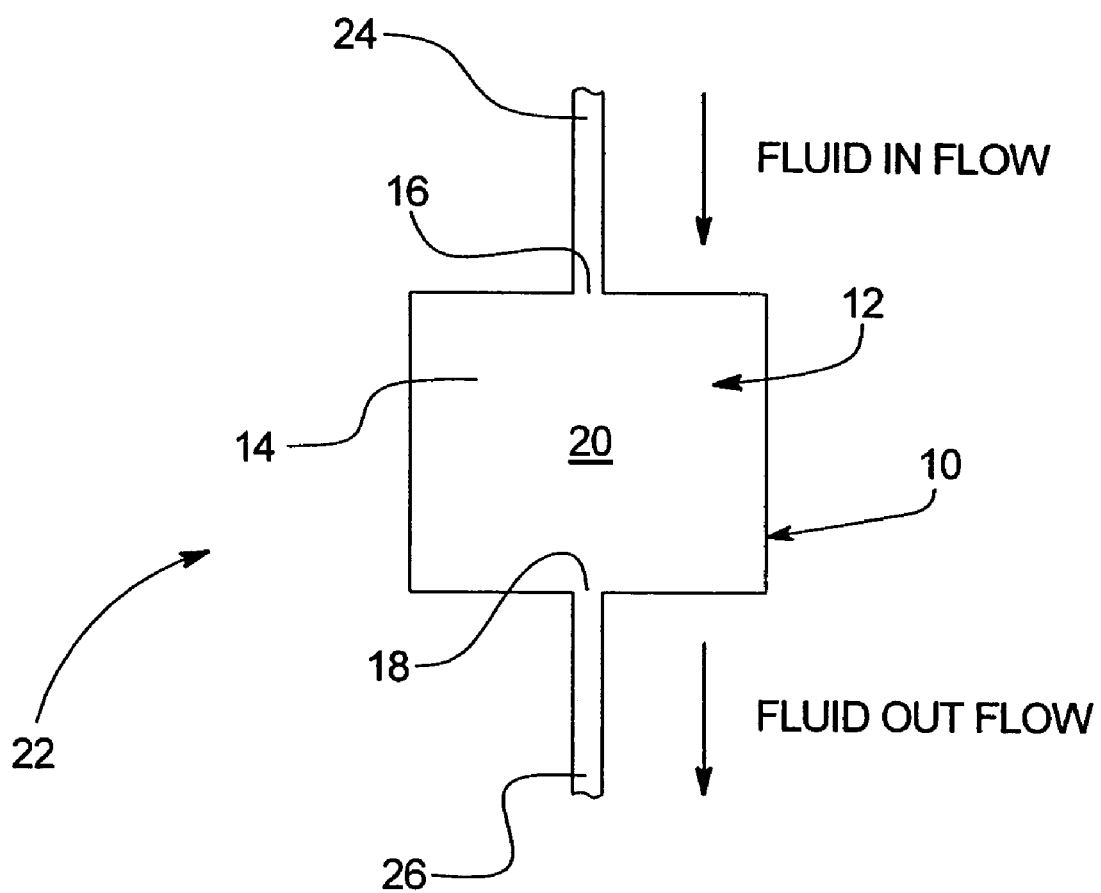
FIG. 1 is a schematic illustration of a system including a device containing a macromolecular composition according to an embodiment of the present invention.

The present invention generally relates to macromolecular compositions. More specifically, the present invention relates to methods of making and using macromolecular compositions, such as those containing ketoaldehydes with chemical binding properties.

In general, the processes of the present invention include the steps of preparing the macromolecular composition, such as a cross-linked polystyrene resin; acetylation of the macromolecular composition; and formation of a ketoaldehyde functional group via oxidation of the acetylated macromolecular composition. The oxidation step, in general, includes the formation of acetyl halide groups and subsequent oxidation thereof to form the ketoaldehyde groups (e.g., glyoxal) in a single reaction step as detailed below. Applicants believe that the processes of the present invention can produce ketoaldehyde-functionalized macromolecular compositions with binding properties with respect to a variety of different constituents in solution as previously discussed.

Applicants believe that the processes of the present invention can result in a higher concentration of active chemical binding sites which correspond to the number of glyoxals on the phenyl ring of the macromolecular composition of the present invention. This can also have the added effect of enhancing the chemical reactivity of the compositions of the present invention with respect to removing constituents, such as urea, from a fluid.

As previously discussed, the process steps of the present invention generally can be described as follows: 1) preparation of resin material; and 2) glyoxalation of resin material. The glyoxalation includes acetylation and subsequent oxidation. It should be appreciated that the processes of the present invention can include any suitable number and type of additional types of reaction steps. For example, the processes of the present invention can include alkylation of the macromolecular composition to provide chemical groups in addition to the ketoaldehyde groups. The additional chemical groups may effect the macromolecular compositions to facilitate the binding properties thereof as discussed above. It should be appreciated that glyoxalation and the addition of the additional chemical groups can occur in any suitable sequence including, for example, during the same process step as described in detail below.

Resin Material Preparation

The present invention can include a variety of suitable resin materials. In general, the resin material can include a porous polymeric structure or non-porous polymeric structure. The pore size can range from microporous to macroporous in size depending on the application. In an embodiment, the resin materials are composed of a porous bead material made from any suitable polymer. Preferably, the resin material is made from cross-linked styrene, such as styrene cross-linked with a suitable amount of a cross-linking agent, such as divinylbenzene. In an embodiment, the cross-linked resin material includes about 25% or less by weight of the cross-linking agent. It should be appreciated that any suitable type of material can be used as the resin material. For example, the resin material can include a gel material. In general, this is a polymeric material that is effectively non-porous.

The resin material of the present invention can be made in any suitable way and/or may be commercially-available. In general, cross-linked polystyrene beads can be made according to known processes, such as suspension polymerization. In a typical reaction, a styrene monomer, divinylbenzene and an initiator are added to a reactor containing an aqueous phase with polymeric and/or inorganic stabilizers. If macroporosity is desired, a precipitant, such as an alkane, can be added to the monomer phase. Optionally, a solvating agent, such as toluene, can be added too. Also, a linear (monomer-soluble) polymer can be used. The reactants are typically stirred and heated to an appropriate temperature to carry out the polymerization reaction.

The resultant polymer can be characterized in a variety of suitable ways. In an embodiment, the styrene content of the polymer ranges from about 0.01% by weight to about 99.9% by weight; and the divinylbenzene content (typically includes a mixture of divinylbenzene and 3-ethyl styrene) ranges from about 0% by weight to about 90% by weight. Preferably, the styrene content is higher than the divinylbenzene content. In an embodiment, the divinylbenzene content ranges from about 0.1% by weight to about 20% by weight. Additional other monomers or polymers in any suitable amount can be present during polymerization. For example, the polymer can include a hydrophilic monomer or its precursor or a hydrophobic monomer in an amount ranging from about 0 to about 10 mole percent or greater. Depending on the application, the resin material of the present invention can include any suitable pore size, surface area and molecular weight.

Glyoxalation

As used herein, the term "glyoxalation" or other like term means modifying a chemical moiety to produce a glyoxal group. For example, modifying a phenyl ring to produce a phenylglyoxal.

In an embodiment, the phenyl group of the polystyrene resin is modified to include the glyoxal group. This can proceed via any suitable reaction mechanism, preferably acetylation via a Friedel Crafts reaction and subsequent oxidation of the acetyl group to form the glyoxal group attached to the phenyl ring. As detailed below, the oxidation step, in an embodiment, can produce the glyoxal group in a single reaction step. In an embodiment, this includes the formation of an acetyl halide group and subsequent oxidation of the acetyl halide group via a reaction with any suitable oxidizing agent, such as, sulfoxide, aliphatic sulfoxides including dimethyl sulfoxide and an acid, such as hydrohalic acid including hydrogen bromide.

Additional Processing

As previously discussed, it should be appreciated that the processes of the present invention are not limited to acetylation and oxidation processing steps but can include any suitable number and types of additional processing steps. For example, chemical groups in addition to the glyoxal groups can be attached to the phenyl ring as previously discussed. These additional other groups can include, for example, electron withdrawing groups, steric groups, chemical groups that can display both steric and electron withdrawing effects, electron donating groups, halogen groups, alkyl groups and/or the like discussed above.

The additional other chemical group(s) can be added to the phenyl ring in any suitable way. For example, the alkyl group(s) can be added to the phenyl ring via alkylation with a typical Friedel Crafts catalyst, alone or in addition to other reaction steps. In general, alkyl halides are known to alkylate benzene to produce alkyl-benzene in the presence of a Lewis acid catalyst, such as ferric chloride or aluminum chloride. Also alkenes in the presence of, for example, hydrochloric acid, trifluoromethane sulfonic acid and a Lewis acid catalyst can be used.

The macromolecular compositions of the present invention can be sterilized in any suitable manner. In an embodiment, the macromolecular compositions can be sterilized with gamma radiation. In general, the composition is exposed to a suitable amount or dose of gamma radiation sufficient for sterilization purposes. In an embodiment, the macromolecular composition of the present invention is exposed to about 5 Gky to about 50 Gky of gamma radiation during sterilization. It should be appreciated that sterilization by gamma radiation can be carried out in any suitable way.

In an embodiment, the macromolecular compositions of the present invention include ketoaldehydes wherein the ketoaldehyde includes a phenyl group and an α-ketoaldehyde group. The produced composition displays chemical binding properties as described below in greater detail. The macromolecular ketoaldehydes can include a hydrated form and/or a non-hydrated form. A general formula that represents a macromolecular phenylketoaldehyde according to an embodiment of the present invention is provided below as follows:

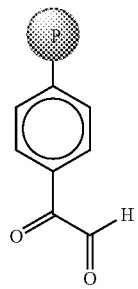

The macromolecular ketoaldehydes of the present invention can effectively remove any suitable number, type and amount of constituents from a solution, such as a physiological solution. The constituents suitable for removal can include, anions, molecules or radicals containing heteroatoms with free electron pairs, such as sulfur, nitrogen and oxygen, such as urea, creatinine, uric acid, β-2 microglobulin, other like metabolic waste, other suitable biological matter and/or the like. It should be appreciated that the macromolecular compositions of the present invention can chemically bind the constituents of any suitable fluid existing in liquid phase, gaseous phase, mixed liquid and gaseous phase, supercritical systems and/or the like.

The chemical binding properties make the macromolecular compositions of the present invention well suited for a variety of different applications subject to physiological and/or non-physiological conditions. In an embodiment, the macromolecular ketoaldehydes of the present invention can be used to remove metabolic waste, such as urea, creatinine, uric acid and/or other like uremic toxins, biological matter, proteinaceous matter, and/or the like from blood and/or solutions used to dialyze blood.

With respect to dialysis therapy, the present invention can be used in a variety of different dialysis therapies to treat kidney failure. Dialysis therapy as the term or like terms are used throughout the text is meant to include and encompass any and all forms of therapies to remove waste, toxins and excess water from the patient. The hemo therapies, such as hemodialysis, hemofiltration and hemodiafiltration, include both intermittent therapies and continuous therapies used for continuous renal replacement therapy (CRRT). The continuous therapies include, for example, slow continuous ultrafiltration (SCUF), continuous venovenous hemofiltration (CVVH), continuous venovenous hemodialysis (CVVHD), continuous venovenous hemodiafiltration (CVVHDF), continuous arteriovenous hemofiltration (CAVH), continuous arteriovenous hemodialysis (CAVHD), continuous arteriovenous hemodiafiltration (CAVHDF), continuous ultrafiltration periodic intermittent hemodialysis or the like. The present invention can also be used during peritoneal dialysis including, for example, continuous ambulatory peritoneal dialysis, automated peritoneal dialysis, continuous flow peritoneal dialysis and the like. Further, although the present invention, in an embodiment, can be utilized in methods providing a dialysis therapy for patients having chronic kidney failure or disease, it should be appreciated that the present invention can be used for acute dialysis needs, for example, in an emergency room setting. However, it should be appreciated that the compositions of the present invention can be effectively utilized with a variety of different applications, physiologic and non-physiologic, in addition to dialysis.

In an embodiment, the marcomolecular compositions of the present invention include macromolecular phenylglyoxals as previously discussed. This type of macromolecular composition includes a phenyl group and a glyoxal group attached to the phenyl group.

It should be appreciated that the glyoxal group can be attached directly or indirectly to the phenyl ring and in any suitable position on the ring. When directly attached, the α-carbon atom of the α-ketoaldehyde can be attached to a carbon atom of the phenyl ring. When indirectly attached, the α-carbon atom of the α-ketoaldehyde is attached to the phenyl ring via a spacer group including, for example, an aliphatic, an alicyclic, an aromatic, substituted or unsubstituted group, and/or the like. In an embodiment, the spacer group includes an aliphatic with 1 to 30 atoms, such as methylene ($CH_2$) or the like, connected to one or a combinations of other suitable chemical groups, such as methyl, ethyl, decyl, phenyl, napthyl or the like.

It should be appreciated that the macromolecular compositions and materials of the present invention can include a variety of other additional constituents in addition to the ketoaldehydes. For example, the present invention can include hydrophilic groups, ion exchanging groups and/or the like depending on the desired application of the present invention, such as for ion exchanging to remove, for example, potassium, controlling the degree of acidity, increasing accessibility in fluid systems and/or the like. To that end, there may be present strongly acid or weakly acid groups or salts thereof, strongly basic or weakly basic groups or salts thereof, and/or hydroxyl groups. Such materials may optionally be pre-charged with, for instance, (earth)alkali(ne) metal ions, such as sodium ions, potassium ions, calcium ions, magnesium ions, chloride ions, bicarbonate ions, acetate ions and/or the like.

By way of example and not limitation, the following examples are illustrative of how to make the macromolecular compositions according to an embodiment of the present invention and further illustrate experimental testing conducted on macromolecular compositions made in accordance with an embodiment of the present invention.

Experiment 1a. General Procedure for the Preparation of Polyvinylacetophenone from Polystyrene-divinylbenzene co-polymer resin (0.5-80% PS/DVB, 5 µm to 1 mm):

To a portion of polystyrene-divinylbenzene co-polymer resin was added dichloroethane or other suitable solvent in a ratio of 1:20 to 1:100 (w/v), which was allowed to swell for a given period of time. To the mixture may be added acetyl chloride during the swelling period. During the swelling the mixture may be heated to assist in swelling. After swelling, 1 to 10 mole equivalence to resin was added acetyl chloride followed by the addition of 1 to 10 mole equivalence of aluminum chloride or other suitable Friedel-Crafts reagent. The reaction was heated at 50° C. to 65° C. for 6 to 24 hours or until the evolution of HCl gas stopped. The resin was isolated by filtration and rinsed with acetone, water, concentrated HCl, water and acetone. The resin was then dried in vacuo at 50° C. to 80° C.

Experiment 1b. General Procedure for the Preparation of Polyvinylacetophenone from Polystyrene-divinylbenzene co-polymer resin(0.5-80% PS/DVB, 5 µm to 1 mm):

To a portion of polystyrene-divinylbenzene co-polymer resin was added dichloroethane or other suitable solvent in a ratio of 1:20 to 1:100 (w/v), which was allowed to swell for a given period of time. To the mixture may be added acetyl chloride during the swelling period. The solvent was removed from the resin, which is not dried. The resin was added to a solution of 1 to 10 mole equivalence of prepared acetyl chloride with aluminum chloride in dichloroethane or other suitable solvent. The reaction was heated 50° C. to 65° C. for 6 to 24 hours or until the evolution of HCl gas as stopped. The resin was isolated by filtration and rinsed with acetone, water, concentrated HCl, water and acetone. The resin was then dried in vacuo at 50° C. to 80° C.

Experiment 2a. General Procedure for the Preparation of α-ketoaldehyde Polystyrene-divinylbenzene Co-Polymer Resin(0.5-80% PS/DVB, 5 µm to 1 mm):

To a portion of polyvinylacetophenone polystyrene-divinylbenzene co-polymer resin was added DMSO (dimethylsulfoxide) solvent in a ratio of 1:1 to 1:100 (w/v), which was allowed to swell for a given period of time. During swelling, the mixture may be heated to assist in swelling. After swelling, 48% HBr (See, Floyd, M. B., et al. *J. Org. Chem.* 1985, 50, 5022-5027) was slowly added at room temperature, after which the temperature was raised to 65° C. to 95° C. and the DMS (dimethyl sulfide) was collected by distillation. After complete distillation of DMS, the reaction was heated to 95° C. or refluxed for an additional 2 to 8 hours. The resin was isolated by filtration, washed successively with water and acetone. The resin was then dried under vacuum at 80° C. for a minimum of 1.5 hours.

Experiment 2b. General Procedure for the Preparation of α-ketoaldehyde Polystyrene-divinylbenzene Copolymer Resin (0.5-80% PS/DVB, 5 µm to 1 mm):

To 12 g of a polyvinylacetophenone polystyrene-divinylbenzene co-polymer resin was added 80 mL of DMSO. Hydrobromic acid (20 mL) was then added at room temperature under gentle stirring. The temperature was then increased to 85° C. for about 8 hours after which time the resin was washed in DMSO, DMSO/acetone mixtures, acetone and water. The resin was dried in an oven at 60° C.

Experiment 3. Urea Uptake Experiment (Batch):

α-ketoaldehyde polymer made in accordance to an embodiment of the present invention was added to a urea solution prepared at 60 mg/dL concentration. The ratio of α-ketoaldehyde polymer to urea solution was kept at 1 gram of α-ketoaldehyde polymer to 100 mL of urea solution. In general, about 500 mg of α-ketoaldehyde polymer was added to 50 mL of urea solution in a sealed pyrex bottle which is mixed for 8 hours at 37° C. The contents of the flask were allowed to cool and the urea concentration of the solution is then measured per Experiment 4 discussed below.

Experiment 4. Measurement of Urea per Urease Method:

Urea concentration from aqueous samples was measured according to the TALKE and SCHUBERT method (See, Talke H and Schubert G E., *Klin Wschr.* 1965;43:174), on a Boehringer Mannheim/Hitachi analyzer.

Experiment 5. COCHO Quantitation:

Quantitation of α-ketoaldehyde groups was determined by a known procedure (See, for example, U.S. Pat. No. 4,012, 317; *Acta Chem. Scand.*, 4, 892-900(1950); and *J. Am. Chem. Soc.*, 94, 1434-1436 (1942). This method is an indirect method of measuring α-ketoaldehyde content, by first converting all α-ketoaldehydes into mandelic acid groups with excess sodium hydroxide. The mmoles of mandelic acid groups is determined by back titration of the excess base with hydrochloric acid to pH 7 and calculating the difference between the amount of base used and the amount titrated.

To 100 mg of resin was added 3 mL of DMSO and 3 mL of 0.5N NaOH with stirring. After 15 minutes, 10 mL of distilled water was added, followed by neutralization of the sodium hydroxide by titration with 0.1N HCl, until the solution stabilized at pH 7.

Experiment 6. General Procedure for the Alkylation of the Polystyrene-divinylbenzene Co-Polymer Resin (0.5-80% PS/DVB, 5 µm to 1 mm):

To a portion of polystyrene-divinylbenzene co-polymer resin was added dichloroethane or other suitable solvent in a ratio of 1:1 to 1:100 (w/v). To the mixture was added 0.1% to 10% nitromethane (v/v) to solvent, followed by the alkyl halide in 0.1 mole to 10 mole equivalence. The mixture was allowed to swell for a given period of time, followed by the addition of $AlCl_3$ (0.1 to 10 mole percent of the resin). The mixture was stirred for 2-4 hours with the temperature ranging from ambient to 50° C. The alkylated resin was isolated by filtration and rinsed with solvent. Acetylation and oxidation to prepare the alkyl α-ketoaldehyde polymer was completed as in Experiments 1b and 2 discussed above. Urea uptake by the resin was completed and measured per Experiments 3 and 4 as previously discussed.

Experiment 7. α-ketoaldehyde Polystyrene-divinylbenzene Co-Polymer Resin Beads (3% PS/DVB, 5 µm to 1 mm per Experiment 1a):

Acetyl chloride (10 mL), 75 mL of dichloroethane, and 10.918 g of resin beads were combined and allowed to swell. The resin beads are commercially available and included 3% by weight of divinylbenzene at a particle size that ranged from 5 pm to 1 mm. The solvent and acetyl chloride were filtered and the resin was combined with 100 mL of dichloroethane, 12 mL of acetyl chloride and 15.310 g of $AlCl_3$. The reaction was heated for 6 hours and the acetylated polymer beads were isolated by filtration, washed with 500 mL of water and 200 mL of acetone. The beads were air dried. 6.200 grams of the acetylated polymer beads were added to 150 mL of DMSO and heated to 80° C., followed by the dropwise addition of 48% HBr. The reaction was heated for 3 hours, and the resin isolated by filtration, rinsed with 200 mL of water and 200 mL of acetone. After air drying, urea uptake value of 47.3 mg of urea/gram of resin was obtained according to Experiments 3 and 4 discussed above.

Experiment 8. α-ketoaldehyde Polystyrene-divinylbenzene Co-Polymer Resin Beads (70-80% PS/DVB per Experiment 1a):

100 g of wet polystyrene resin beads (Supelco, Amberlite XAD-4) were dried by eluting THF through the resin beads. The resin beads are commercially available and included 70% by weight to 80% by weight of divinylbenzene at a particle size that ranged from 5 µm to 1 mm. The resin beads were then rinsed with 2×150 mL portions of dichloroethane. The resin beads were swollen with 300 mL of dichloroethane and 50 mL of acetyl chloride. The solution was decanted and 500 mL of fresh dichloroethane with 100 mL of acetyl chloride were combined with the resin followed by 147.38 grams of $AlCl_3$. The reaction was heated to 42° C. for 48 hours. The resin beads were isolated by filtration and rinsed with 4 L water containing 750 mL concentrated HCl over a period of 3 to 5 hours. The resin was rinsed with 2 L of water followed by 1 L of DMSO. The resin beads were transferred to a reaction flask with 500 mL of DMSO, and 200 mL of 48% HBr. The mixture was heated to reflux and mixed for 24 hours. The resin beads were isolated by filtration, rinsed with 4 L of water over 2 hours, and dried at 80 ° C. in vacuum for 3 hours. After drying, urea uptake value of 8.8 mg of urea/gram of resin was obtained as performed by Experiments 3 and 4.

Experiment 9. α-ketoaldehyde Polystyrene-divinylbenzene Co-Polymer Resin Beads (PS/1% DVB, per experiment 1b):

Preparation of the polystyrene-divinylbenzene co-polymer beads was accomplished by placing the polymer resin beads (2.5 g) in a dry 300 mL three necked flask with 40 mL of dichloroethane, and 15 mL of acetyl chloride for 3 hours. The swelled polymer was rinsed with excess dichloroethane and isolated by filtration. To a separate dry round bottom 300 mL flask was added 25 mL of dichloroethane, 7 g of $AlCl_3$, and 4.5 mL of acetyl chloride. The mixture was allowed to dissolve, followed by the addition of the previously swelled resin. The mixture was allowed to react at 65 to 75° C., for 14 hours with constant stirring. The resin was isolated by filtration, and rinsed by the following procedure. First with 300 mL of dichloroethane, 400 mL of acetone, 300 mL of water, 300 mL of water with 90 mL of concentrated HCl, 600-800 mL of water and a final rinse with 150 mL of acetone. The acetylated polymer was dried in vacuo. The acetylated resin was transferred into 250 mL flask with 30 mL of DMSO (dimethylsulfoxide), and soaked at 80-90° C. for 30-45 minutes. To the reaction was added 10 mL of HBr dropwise, and heated for 2 hours. The reaction was refluxed for another two hours, cooled, rinsed with DMSO, water, acetone and isolated by filtration. The α-ketoaldehyde PS/1% DVB polymer beads were dried in vacuo had a urea uptake of 45 mg of urea/gram of α-ketoaldehyde polymer according to Experiments 3 and 4.

Experiment 10. Scale-up Acetylation of 1% PS/DVB Beads to Produce Polyacetophenone:

Preparation of the Polystyrene-divinylbenzene (1% PS/DVB, 75 to 150 mesh) co-polymer beads was accomplished by placing the polymer resin beads in a dry 1 L three necked flask with 600 mL of dichloroethane, 200 mL of acetyl chloride, and 45 g of the polymer. After 3 hours, the polymer resin was isolated by filtration and washed with excess dichloroethane. To a dry round bottom lL flask was added 500 mL of dichloroethane, 146 g of $AlCl_3$, and 100 mL of acetyl chloride. The mixture was allowed to dissolve, followed by the addition of 100 mL of dichloroethane at 65 to 75° C. The previously swelled resin was slowly added to the solution and allowed to react at 65 to 75° C., for 14 hours with gentle stirring. The resin was isolated by filtration, and rinsed with dichloroethane. The resin was washed and isolated by filtration with 600 mL of dichloroethane, excess acetone and 23% HCl solution. The final water rinse was checked at neutral pH before the final rinse with 500 mL of acetone.

Experiment 11. Preparation of α-ketoaldehyde 1% PS/DVB Beads:

To a dry 2 L 3-necked round bottom flask was added 240 mL of DMSO (dimethylsulfoxide) and 16 grams of acetylated resin from Experiment 10. The reaction mixture was mixed for 45-60 minutes at 80° C. to 90° C. under gentle stirring. To the mixture was added 80 mL of 48% hydrobromic acid while distilling off dimethylsulfide for two hours. The reaction was allowed to reflux for an additional 2 hours. The reaction was allowed to cool and the α-ketoaldehyde 1% PS/DVB beads were isolated by filtration, washed successively with water and acetone. The resin was then dried under vacuum at 80° C. for a minimum of 1.5 hours. The α-ketoaldehyde PS/1% DVB polymer beads were dried in vacuo and had a urea uptake of 39.6 mg of urea/gram of α-ketoaldehyde polymer according to Experiments 3 and 4.

Experiment 12. Urea Uptake Test I:

Several polystyrene resin beads with varying amounts of DVB were prepared according to Experiments 7, 8, and 9 with urea uptake results according to Experiments 3 and 4. The results are shown below in Table 1.

TABLE 1

Urea Uptake of α-ketoaldehyde resin per experiment 12

| Experiment | Uptake of Urea in mg/g of urea/polymer | mmol α-ketoaldehyde per gram of resin | % DVB Content |
|---|---|---|---|
| 8 | 8.8 | 2.45 | 70-80 |
| 7 | 20.8 | 3.1 | 3 |
| 9 | 47.3 | 3.1 | 3 |
| 9 | 45 | 5.9 | 1 |

Experiment 13. Gamma Radiation of α-ketoaldehyde Resins:

This experiment was conducted to determine the effect of gamma radiation on urea uptake. A resin material made pursuant to an embodiment of the present invention was determined to have an urea uptake value of 43.8 mg of urea per gram of resin pursuant to Experiments 3 and 4. The same resin material was exposed to about 40 Gky to about 50 Gky gamma radiation and an urea uptake value of 43.6 mg of urea per gram of resin was obtained according to Experiments 3 and 4.

Experiment 14. Urea Uptake Test II:

To 50 mL of a 505.8 mg/dL urea solution was added 0.507 g of α-ketoaldehyde polymer prepared similar to experiment 10. The mixture was sealed in a pyrex bottle and heated to 50° C. with stirring for 24 hours. The urea concentration was measured as per Experiment 4, and the α-ketoaldehyde polymer had a urea uptake of 109 mg of urea per gram of α-ketoaldehyde polymer.

Experiment 15. Urea Uptake Test III:

Urea uptake by the α-ketoaldehyde polymer prepared as in Experiment 9 was measured per the procedure in Examples 11 to 15 according to U.S. Pat. No. 4,012,317. 100 mg of polymer and 15 mL of an aqueous solution of urea of concentration 1 g/L, were mixed with either a solution of 0.05 molar monopotassium phosphate (pH 7) or a solution of 0.05 mol/L sodium carbonate and bicarbonate at pH 10. The contents of the sealed bottles were mixed for 15 hours at 37° C. with samples prepared in duplicate and results averaged. Urea uptake was measured per Experiment 4. The results are shown below in Table 2.

TABLE 2

Urea Uptake Comparison - 1 g/L Urea

| α-ketoaldehyde polymer | Urea uptake in mg/g of polymer | Mmol of α-ketoaldehyde per gram of resin | pH of urea solution | Time (hours) |
|---|---|---|---|---|
| 1 | 3.2 | 3.3 | 7 | 2.5 |
| 1 | 19.8 | 3.3 | 7 | 15 |
| 1 | 4.0 | 3.3 | 10 | 2.5 |
| 1 | 12.8 | 3.3 | 10 | 15 |
| 2 | 7.5 | 3.6 | 10 | 15 |

1. α-ketoaldehyde polymer prepared according to Experiment 9.
2. α-ketoaldehyde polymer prepared according to example 3 of U.S. Pat. No. 4,012,317.

Experiment 16. Urea Uptake Test IV:

Urea uptake by the α-ketoaldehyde polymer prepared in Experiment 9 was measured per the procedure in Example 5 from U.S. Pat. No. 4,012,317. 25 mg of α-ketoaldehyde polymer was combined with 5 mL of an aqueous solution of urea of concentration of 1 mol/l and 5 mL of solution containing either 0.05 molar monopotassium phosphate (pH 7) or 5 mL of a solution of 0.05 mol/L sodium carbonate and bicarbonate at pH 10. The contents of the sealed pyrex bottles were mixed for 15 hours at 37° C., filtered and washed 10 times with 20 mL aliquots of water. The resins were then dried under vacuo. Urea in the α-ketoaldehyde polymer measured as percent nitrogen by elemental analysis. Results in Table 3 provide a comparison of results from the α-ketoaldehyde polymer prepared in U.S. Pat. No. 4,012,317 as indicated below.

TABLE 3

Urea Uptake Comparison - 0.5 mol/L Urea Concentration

| α-ketoaldehyde polymer | Urea uptake in mg/g of polymer | % Nitrogen Measured in the α-ketoaldehyde Polymer | mmol of α-ketoaldehyde per gram of resin | pH of urea solution | Time (hours) |
|---|---|---|---|---|---|
| 1 | 90 | 3.48 | 3.14 | 7 | 15 |
| 1 | 79 | 3.05 | 3.14 | 10 | 15 |
| 2 | 17.15 | 2.4[3] | 3.6 | 7 | 15 |
| 2 | 30 | 2.87[3] | 3.6 | 10 | 15 |

1. α-ketoaldehyde polymer prepared according to Experiment 9, with a urea uptake of 47.3 mg urea/gram of polymer per Experiments 3 and 4.
2. α-ketoaldehyde polymer prepared in U.S. Pat. No. 4,012,317 according to example 3.
[3]Percent Nitrogen Value based on urea uptake from U.S. Pat. No. 4,012,317, example 6.

As previously discussed, the present invention provides materials, devices, apparatuses and systems that can utilize macromolecular ketoaldehyde compositions made pursuant to an embodiment of the present invention. The macromolecular compositions of the present invention are particularly suited for removing urea or the like under physiological conditions, such as from solutions used during dialysis therapy. The binder materials of the present invention can include any suitable type of material including, for example, a porous bead material composed of cross-linked polystyrene that has been modified to include a phenyl ring, an α-ketoaldehyde group and, optionally, one or more activating chemical groups attached to the phenyl ring in proximity to the α-ketoaldehyde group. In an embodiment, the urea binder material of the present invention can remove urea from a fluid, such as a dialysis fluid during dialysis therapy.

In an embodiment, the present invention includes devices that utilize the urea binder material made pursuant to an embodiment of the present invention to remove urea in solution. In general, the device 10 includes a body 12 defining an interior 14 through which a fluid can pass into the device 10 via an inlet 16 and optionally flow out of the device via an outlet 18 as shown in FIG. 1. The device 10 contains the urea binder material 20 of the present invention in its interior 14. The device 10 can contain the urea binder material in any suitable way, such as in a layered configuration. As the fluid passes through the device, the urea binder material acts to remove urea from the fluid.

As applied, the device is particularly suited for removal of urea from a dialysis solution during dialysis therapy. In an embodiment, the device includes a chemical cartridge coupled in any suitable manner to a patient loop through which dialysate is circulated into, through and out of the patient during dialysis therapy, such as continuous flow peritoneal dialysis. In this regard, the device can be used to remove a therapeutically effective amount of urea from the dialysis solution as it continually passes through the device prior to circulation into, through and out of the patient. This can enhance dialysis clearance and minimize the amount of dialysis fluid necessary to maintain effective clearance levels during dialysis therapy. In an embodiment, the urea binder device can remove urea from solution used during medical therapy, such as dialysis. To achieve an effective urea uptake, the device, in an embodiment, includes about 500 g or less of the macromolecular material made in accordance to an embodiment of the present invention.

It should be appreciated that the chemical cartridge can include any suitable number, type and amount of materials in addition to a urea binder material in order to enhance treatment. For example, the chemical cartridge can include a carbon layer for removal of creatinine, β2-microglobulin and/or the like, a material layer to remove phosphate and/or the like and the urea binder material to remove urea and/or the like.

As previously discussed, the present invention provides a system capable of removing a constituent from a fluid. The system can be applied in a variety of different applications including, for example, therapeutic and diagnostic applications. In an embodiment, the system 22 includes a fluid pathway through which the fluid can flow that is coupled to the device 10 as discussed above and as shown in FIG. 1. The fluid pathway at least includes an inflow fluid path 24 allowing fluid to enter the device. Optionally, a number of other suitable fluid pathways can be coupled to the device, such as an outflow fluid path 26 allowing the fluid to pass through and out of the device 10.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A macromolecular composition comprising:
   polystyrene;
   a spacer group attached to a phenyl group of the polystyrene, wherein the spacer group is selected from the group consisting of a substituted or an unsubstituted aliphatic group, a substituted or an unsubstituted alicyclic group, a substituted or an unsubstituted aromatic group and combinations thereof; and
   an alpha-ketoaldehyde group attached to the spacer group.

2. A macromolecular composition comprising:
   polystyrene;
   a spacer group attached to a phenyl group of the polystyrene, wherein the spacer group comprises a methylene group; and
   an alpha-ketoaldehyde group attached to the spacer group.

* * * * *